(12) United States Patent
Huval et al.

(10) Patent No.: US 7,638,524 B2
(45) Date of Patent: Dec. 29, 2009

(54) COMBINATION THERAPY FOR TREATING HYPERCHOLESTEROLEMIA

(75) Inventors: Chad Cori Huval, Somerville, MA (US); Stephen Randall Holmes-Farley, Arlington, MA (US); John S. Petersen, Acton, MA (US); Pradeep K. Dhal, Westford, MA (US)

(73) Assignee: Genzyme Corporation, Waltham, MA (US)

( * ) Notice: Subject to any disclaimer, the term of this patent is extended or adjusted under 35 U.S.C. 154(b) by 576 days.

(21) Appl. No.: 10/025,184

(22) Filed: Dec. 19, 2001

(65) Prior Publication Data

US 2002/0155091 A1     Oct. 24, 2002

Related U.S. Application Data

(63) Continuation of application No. 09/311,103, filed on May 13, 1999, now Pat. No. 6,365,186, which is a continuation-in-part of application No. 08/964,536, filed on Nov. 5, 1997, now Pat. No. 6,083,497.

(51) Int. Cl.
| | |
|---|---|
| A61K 9/14 | (2006.01) |
| A61K 9/00 | (2006.01) |
| A61K 31/785 | (2006.01) |
| A61K 31/795 | (2006.01) |
| A01N 43/40 | (2006.01) |
| A61K 31/435 | (2006.01) |
| A01N 43/64 | (2006.01) |
| A61K 31/41 | (2006.01) |

(52) U.S. Cl. .............. 514/277; 424/78.35; 424/78.14; 424/78.15; 424/400; 424/486; 514/359

(58) Field of Classification Search .............. 424/78.35, 424/464–65, 451, 439, 401, 486, 400, 78.14, 424/78.15; 514/824, 277, 359
See application file for complete search history.

(56) References Cited

U.S. PATENT DOCUMENTS

| | | | |
|---|---|---|---|
| 2,926,161 A | 2/1960 | Butler et al. ............... 260/89.7 |
| 3,262,850 A | 7/1966 | Jones et al. ................... 167/65 |
| 3,288,770 A | 11/1966 | Butler ........................ 260/88.3 |
| 3,369,025 A | 2/1968 | Bolhofer et al. ............. 260/295 |
| 3,494,957 A | 2/1970 | Nakanishi et al. ............ 260/473 |
| 3,607,909 A | 9/1971 | Boulogene et al. ....... 260/477 R |
| 3,674,836 A | 7/1972 | Creger ................... 260/473 G |
| 3,700,623 A * | 10/1972 | Keim et al. ............... 525/328.3 |
| 3,716,583 A | 2/1973 | Nakamura et al. .......... 260/520 |
| 3,723,446 A | 3/1973 | Scherm et al. ........ 260/295.5 R |
| 3,781,328 A | 12/1973 | Witte et al. ............. 260/471 R |
| 3,833,531 A | 9/1974 | Keim ................. 260/29.6 CM |
| 3,840,504 A | 10/1974 | Keim ..................... 260/79.3 A |
| 3,948,973 A | 4/1976 | Phillips ...................... 260/473 |
| 3,966,694 A | 6/1976 | Espy et al. ................ 526/11.2 |
| 3,971,798 A | 7/1976 | Humbert et al. ............. 260/295 |
| 3,983,140 A | 9/1976 | Endo et al. ................ 260/343.5 |
| 3,984,413 A | 10/1976 | Metz et al. ................... 260/254 |
| 3,990,958 A | 11/1976 | Sasse ..................... 204/159.22 |
| 4,049,813 A | 9/1977 | Nadelson ..................... 424/263 |
| 4,058,552 A | 11/1977 | Mieville ....................... 560/52 |
| 4,121,986 A | 10/1978 | Battaerd ................. 204/159.22 |
| 4,167,610 A | 9/1979 | Bolto et al. |
| 4,230,626 A | 10/1980 | Chorvat ................... 260/397.2 |
| 4,231,938 A | 11/1980 | Monaghan et al. ........ 260/343.5 |
| 4,298,715 A | 11/1981 | Van Eenam ................. 525/340 |
| 4,346,227 A | 8/1982 | Terahara et al. ............. 560/119 |
| 4,444,784 A | 4/1984 | Hoffman et al. ............. 424/279 |
| 4,450,171 A | 5/1984 | Hoffman et al. ............. 424/279 |
| 4,452,957 A | 6/1984 | Neigel .......................... 526/71 |
| 4,483,999 A | 11/1984 | Thiele et al. .................. 560/57 |
| 4,604,217 A * | 8/1986 | Lukach et al. |
| 4,659,474 A * | 4/1987 | Perry et al. |
| 4,739,073 A | 4/1988 | Kathawala ................... 548/406 |
| 4,759,923 A | 7/1988 | Buntin et al. ................ 424/440 |
| 4,812,540 A | 3/1989 | Kageno et al. ............ 526/218.1 |
| 4,937,259 A | 6/1990 | Lee ............................ 514/460 |
| 5,134,155 A | 7/1992 | Connolly et al. ............. 514/403 |
| 5,200,482 A | 4/1993 | Gartner ...................... 526/295 |
| 5,273,995 A | 12/1993 | Roth ........................... 514/422 |

(Continued)

FOREIGN PATENT DOCUMENTS

| | | |
|---|---|---|
| CA | 2007641 | 8/1990 |

(Continued)

OTHER PUBLICATIONS

McCarthy, P.A., "New Approaches to Atherosclerosis: An Overview," *Medicinal Research Reviews*, 13(2):139-159 (1993).

(Continued)

*Primary Examiner*—Sreeni Padmanabhan
*Assistant Examiner*—Kara R McMillian
(74) *Attorney, Agent, or Firm*—Hamilton, Brook, Smith & Reynolds, P.C.

(57) ABSTRACT

The invention relates to methods for treating hypercholesterolemia and atherosclerosis, and reducing serum cholesterol in a mammal. The methods of the invention comprise administering to a mammal a first amount of a bile acid sequestrant compound which is an unsubstituted polydiallylamine polymer and a second amount of a cholesterol-lowering agent. The first and second amounts together comprise a therapeutically effective amount.

The invention further relates to pharmaceutical compositions useful for the treatment of hypercholesterolemia and atherosclerosis, and for reducing serum cholesterol. The pharmaceutical compositions comprise a combination of a first amount of an unsubstituted polydiallylamine polymer compound and a second amount of a cholesterol-lowering agent. The first and second amounts comprise a therapeutically effective amount. The pharmaceutical compositions of the present invention may optionally contain a pharmaceutically acceptable carrier.

10 Claims, No Drawings

U.S. PATENT DOCUMENTS

| | | | |
|---|---|---|---|
| 5,274,155 A | 12/1993 | Thottathil et al. | 556/405 |
| 5,316,765 A | 5/1994 | Folkers et al. | 424/94.1 |
| 5,428,112 A | 6/1995 | Ahlers et al. | 525/326.7 |
| 5,430,110 A | 7/1995 | Ahlers et al. | 525/328.2 |
| 5,462,730 A * | 10/1995 | McTaggart et al. | 424/78.35 |
| 5,556,619 A | 9/1996 | Royce et al. | 424/78.08 |
| 5,607,669 A | 3/1997 | Mandeville, III et al. | 424/78.12 |
| 5,618,530 A | 4/1997 | Mandeville, III et al. | 424/78.12 |
| 5,624,963 A | 4/1997 | Mandeville, III et al. | 514/789 |
| 5,633,344 A | 5/1997 | Figuly | 528/397 |
| 5,679,717 A | 10/1997 | Mandeville, III et al. | 514/742 |
| 5,693,675 A | 12/1997 | Mandeville, III et al. | 514/742 |
| 5,703,188 A | 12/1997 | Mandeville, III et al. | 526/290 |
| 5,874,522 A | 2/1999 | Figuly et al. | 528/422 |
| 6,083,497 A * | 7/2000 | Huval et al. | 424/78.35 |
| 6,203,785 B1 * | 3/2001 | Holmes-Farley et al. | 424/78.18 |
| 6,248,318 B1 * | 6/2001 | Huval et al. | 424/78.35 |
| 6,264,938 B1 * | 7/2001 | Huval et al. | 424/78.35 |

FOREIGN PATENT DOCUMENTS

| | | |
|---|---|---|
| CA | 2016467 | 12/1990 |
| DE | 2038835 | 2/1971 |
| DE | 2149070 | 4/1973 |
| DE | 2250327 | 4/1973 |
| DE | 3122499 | 12/1981 |
| EP | 0794053 A2 | 9/1964 |
| EP | 22478 B1 | 1/1981 |
| EP | 33538 B1 | 8/1981 |
| EP | 244364 | 11/1987 |
| EP | 245003 | 11/1987 |
| EP | 321090 | 6/1989 |
| EP | 329 124 | 8/1989 |
| EP | 326386 | 8/1989 |
| EP | 369323 | 5/1990 |
| EP | 0 375 350 A2 | 6/1990 |
| EP | 380392 B1 | 8/1990 |
| EP | 409281 | 1/1991 |
| EP | 418648 B1 | 3/1991 |
| EP | 464845 B1 | 1/1992 |
| EP | 0 580 078 A1 | 1/1994 |
| EP | 0 580 079 A1 | 1/1994 |
| EP | 0 665 245 A1 | 8/1995 |
| GB | 860303 | 2/1961 |
| GB | 2 090 605 A | 7/1982 |
| GB | 2270312 | 3/1994 |
| GB | 2 29 334 | 3/1999 |
| JP | 56-51992 | 5/1981 |
| JP | 3-109407 | 5/1991 |
| JP | 7-89898 | 4/1995 |
| JP | 8-73432 | 3/1996 |
| WO | WO 90/00897 | 2/1990 |
| WO | WO 95/34585 | 12/1995 |
| WO | WO 98/29107 | 7/1998 |
| WO | WO 98/40375 | 9/1998 |

OTHER PUBLICATIONS

Heming, A.E. and Flanagan, T.L., "Considerations in the Selection of Cation Exchange Resins for Therapeutic Use," *In Annals of the New York Academy of Sciences*, 57:239-251 (1954).

Harada, Susumu and Kunio Arai, "The Cyclo-copolymerization of Diallyl Compounds and Sulfur Dioxide, II. Diallyldimethylammonium Chloride and Sulfur Dioxide," *Die Makromolekulare Chemie* 107:64-77 (1967).

Negi, Youji et al., "Cyclopolymerization of Diallylamine Derivatives in Dimethyl Sulfoxide," *Journal of Polymer Science: Part A-1*, 5:1951-1965 (1967).

Kuron, G.W. et al., "The Bile Acid Binding and Hypocholesterolemic Action of Two Water-soluable Polymers," *Atherosclerosis* 37:353-360 (1980).

Hodgkin, J.H. et al., "Use of $^{13}$C-NMR in the Study of Reactions on Crosslinked Resins," *Journal of Polymer Science* 19(5):1239-1249 (1981).

U.S. Appl. No. 08/777,408, filed Dec. 30, 1996, "Poly (diallylamine)—Based Bile Acid Sequestrant" by Stephen Randall Holmes-Farley, Pradeep K. Dhal and John S. Petersen.

Sit, S.Y., et al., "Synthesis, Biological Profile, and Quantitative Structure-Activity Relationship of a Series of Novel 3-Hydroxy-3-methylglutaryl Coenzyme A Reductase Inhibitors," *J. Med. Chem.*, 33(11), 2982-99 (1990).

Takano, S., et al., "Enanticonvergent Synthesis of a Promising HMG Co-A Reductase Inhibitor NK-104 from Both Enantiomers of Epichlorohydrin," *Tetrahedron:Assymetry*, 4(2), 201-4 (1993).

Sood, A., et al., "Boron analogues of amino acids VI. Synthesis and characterization of di- and tripeptide analogues as antineoplastic, anti-flammatory and hypolipidemic agents," *Eur. J. Med. Chem.*, 25(4), 301-8 (1990).

Raulston, D.L., et al., "Inhibition of Hepatic Sterol Synthesis and Reduction of Serum Cholesterol in Rats by 5α-Cholest-8(14)-En-3β-O1-15-One," *Biochem. Biophys. Res. Commun.*, 71(4), 984-9 (1976).

Wint, L.T. and McCarthy, P.A., "Synthesis of Tritium Labelled (3R*,5S*) -3,5-Dihydroxy-9,9-diphenyl-6,8-nonadienoate," *J. Labelled Compd. Radiopharm.*, 25(11), 1289-97 (1988).

Falck, J.R. and Yang, Y.-L., "Total Synthesis of (+)-Dihydromevinolin," *Tetrahedron Lett.*, 25(33), 3563-66 (1984).

Beck, G., et al., "Synthesis and Biological Activity of New HMG-CoA Reductase Inhibitors. 1.Lactones of Pyridine- and Pyrimidine-Substituted 3,5-Dihydroxy-6-heptenoic (-heptanoic) Acids," *J. Med. Chem.*, 33(1), 52-60 (1990).

Jendralla, H., et al., "Synthesis and Biological Activity of New HMG-CoA Reductase Inhibitors. 3.$^{1,2}$ Lactones of 6-Phenoxy-3,5-dihydroxyhexanoic Acids," *J. Med. Chem.*, 34(10) 2962-83 (1991).

Chiang, Y.-C.P., et al., "Total Synthesis of L-659,699, a Novel Inhibitor of Cholesterol Biosynthesis," *J. Org. Chem.*, 54(24), 5708-12 (1989).

Ogawa, H., et al., "Pannorin, A New 3-Hydroxy-3-Methylglutaryl Coenzyme A Reductase Inhibitor Produced by *Chrysosporium pannorum*," *J. Antibiot.*, 44(7), 762-7 (1991).

Carte, B.K., et al., "Rawsonol, An Inhibitor of HMG-CoA Reductase from the Tropical Green Alga *Avrainvillea rawsoni*," *Phytochemistry*, 28(11), 2917-19 (1989).

Baumann, K.L., et al., "The Convergent Synthesis of CI-981, an Optically Active, Highly Potent, Tissue Selective Inhibitor of HMG-CoA Reductase," *Tetrahedron Lett.*, 33(17), 2283-4 (1992).

Larsen, S.D., et al., "Design and Synthesis of Seco-oxysterol Analogs as Potential Inhibitors of 3-Hydroxy-3-methylglutaryl-Coenzyme A (HMG-CoA) Reductase Gene Transcription," *J. Med. Chem.*, 37(15), 2343-51 (1994).

Kumar, N., et al., "Separation of 3-hydroxy-3-methylglutaryl-coenzyme A reductase inhibitor drug substance diastereomers, and their analogues on β-cyclodextrin stationary phase," *J. Chromatrogr. A*, 678(2), 259-63 (1994).

Stokker, G.E., "Synthesis of L-669,262, a Potent HMG-CoA Reductase Inhibitor," *J. Org. Chem.*, 59(20), 5983-6 (1994).

Kramer, W., et al., "Bile Acid Derived HMG-CoA Reductase Inhibitors," *Biochimica et Biophysica Acta*, 1227(3), 137-54 (1994).

Huang, Y. and Hall, I.H., "Hypolipidemic Effects of α, β, and γ-Alkylaminophenone Analogs in Rodents," *Eur. J. Med. Chem.*, 31(4), 281-90 (1996).

Huang, Y. and Hall, I.H., "Hypolipidemic Activity of 3-Amino-1-(2,3,4-mononitro-, mono-, or dihalophenyl)propan-1-ones in Rodents," *Arch. Pharm., Pharm. Med. Chem.* 329(7), 339-346 (1996).

Watanabe, S., et al., "Synthesis of 4-[1-(substituted phenyl)-2-oxo-pyrrolidin-4-yl]methyloxybenzoic acids and related compounds, and their inhibitory capacities toward fatty-acid and sterol biosyntheses," *Eur. J. Med. Chem.*, 29(9), 675-86 (1994).

Hermecz, I., et al., "Synthesis of anti-atherosclerotic pyrido[1,2-a]pyrimidines," *Arzneim-Forsch*, 29(12), 1833-5 (1979).

Ko, S.S., et al., "Synthesis and HMG-CoA Reductase Suppression and LDL Receptor Induction Activities of DMP 565 and Related 15-Oxasterols," *Abstr. #10 Papers Am. Chem. Soc.* (207$^{th}$ National Meeting, Part 1, MEDI 10, 1994).

Abstract for Accession No. 90-233170/199031 from World Patent Index Database compiled by Derwent Information Limited.

Abstract for Accession No. 91-088314/199113 from World Patent Index Database compiled by Derwent Information Limited.

Abstract for Accession No. 81-93634D/198151 from World Patent Index Database compiled by Derwent Information Limited.

Abstract for Accession No. 71-08176S/197104 from World Patent Index Database compiled by Derwent Information Limited.

Abstract for Accession No. 73-15504U/197311 from World Patent Index Database compiled by Derwent Information Limited.

Abstract for Accession No. 73-21400U/197316 from World Patent Index Database compiled by Derwent Information Limited.

Abstract for Accession No. 81-46770D/198126 from World Patent Index Database compiled by Derwent Information Limited.

Abstract for Accession No. 96-205496/199621 from World Patent Index Database compiled by Derwent Information Limited.

Abstract for Accession No. 95-167208/199522 from World Patent Index Database compiled by Derwent Information Limited.

Abstract for Accession No. 3-109407/199125 from World Patent Index Database compiled by Derwent Information Limited.

* cited by examiner

COMBINATION THERAPY FOR TREATING HYPERCHOLESTEROLEMIA

RELATED APPLICATIONS

This application is a Continuation of U.S. Ser. No. 09/311,103, filed on May 13, 1999, now U.S. Pat. No. 6,365,186 which is a Continuation-in-Part of U.S. Ser. No. 08/964,536, filed on Nov. 5, 1997, now U.S. Pat. No. 6,083,497. The entire teachings of the above documents are incorporated herein by reference.

BACKGROUND OF THE INVENTION

Reabsorption of bile acids from the intestine conserves lipoprotein cholesterol in the bloodstream. Conversely, blood cholesterol levels can be diminished by reducing reabsorption of bile acids.

One method of reducing the amount of bile acids that are reabsorbed and, thus, reducing serum cholesterol is the oral administration of compounds that sequester the bile acids and cannot themselves be absorbed. The sequestered bile acids are excreted.

Compounds which have been suggested for bile acid sequestration include various ion exchange polymers. One such polymer is cholestyramine, a copolymer of divinylbenzene and trimethylammoniummethyl styrene. It has been long recognized that this polymer is unpalatable, gritty, and constipating. More recently, various polymers have been suggested which are characterized by hydrophobic substituents and quaternary ammonium radicals substituted upon an amine polymer backbone (Ahlers, et al. U.S. Pat. Nos. 5,428,112 and 5,430,110 and McTaggart, et al., U.S. Pat. No. 5,462,730, which are incorporated herein by reference). In some cases, these polymers have had disappointing efficacy and require complex processes for their manufacture.

Fibrates are also a known class of compounds which has been used as cholesterol-lowering agents. Fibrates are peroxisome proliferator-activated receptor antagonist that effectively lower plasma triglycerides by increasing VLDL lipolysis and clearance, and by decreasing hepatic VLDL triglyceride output. Fibrate treatment also raises HDL levels by increasing hepatic HDL synthesis. Examples of fibrates include, Clofibrate (ATROMID-S®), Gemfibrozil (LOPID®), Fenofibrate, Benzafibrate and the compounds listed in Table 1.

Another class of compounds which have been used as cholesterol-lowering agents are nicotinic acid, commonly referred to as niacin, and derivatives thereof. Niacin is a potent triglyceride reducing agent with an HDL-elevating effect. Niacin therapy is prescribed to treat patients with moderate to severe hypertriglyceridemia and does not usually produce a significant LDL cholesterol-lowering effect. Niacin acts within the liver to decrease VLDL triglyceride output and in the periphery to increase its clearance. The side effects of niacin are well-known and usually limit usage. For example, high doses cause pruritis and flushing. In addition, an elevation in liver enzymes, abdominal cramps, diarrhea, nausea and vomiting have been observed. Niacin is available, for example, as NICOLAR® tablets. Nicotinic acid derivatives include, Acipimox, Aluminum Nicotinate, Niceritrol, Nicoclonate, Nicomol and Oxiniacic Acid.

Another class of compounds which are useful in cholesterol-lowering therapy are thyroid hormones and analogs such as Etiroxate, Thyropropic Acid and Thyroxine.

In addition, there are many known cholesterol-lowering agents which are not members of a particular class of agents. These other cholesterol-lowering agents include, Acifran, Azacosterol, Benfluorex, β-Benzalbutyramide, Carnitine, Chondroitin Sulfate, Clomestrone, Detaxtran, Dextran Sulfate Sodium, 5,8,11,14,17-Eicosapentaenoic Acid, Eritadenine, Furazabol, Meglutol, Melinamide, Mytatrienediol, Ornithine, γ-Oryzanol, Pantethine, Pentaerythritol Tetraacetate, α-phenybutyramide, Priozadil, Probucol, B-Sitosterol, Sultosilic Acid, Piperazine Salt, Tiadenol, Triparanol and Xenbucin.

The present invention furthers efforts for treating hypercholesterolemia and atherosclerosis, as well reducing serum cholesterol, by providing a combination therapy approach and a novel pharmaceutical composition useful therefor.

SUMMARY OF THE INVENTION

The invention relates to methods for treating hypercholesterolemia and atherosclerosis, and reducing serum cholesterol in a mammal. The methods of the invention comprise administering to a mammal a first amount of a bile acid sequestrant compound which is an unsubstituted polydiallylamine polymer and a second amount of a cholesterol-lowering agent selected from the group consisting of fibrates, nicotinic acid and derivatives thereof, and other cholesterol-lowering agents such as Acifran, Azacosterol, Benfluorex, β-Benzalbutyramide, Carnitine, Chondroitin Sulfate, Clomestrone, Detaxtran, Dextran Sulfate Sodium, 5,8,11,14,17-Eicosapentaenoic Acid, Eritadenine, Furazabol, Meglutol, Melinamide, Mytatrienediol, Ornithine, γ-Oryzanol, Pantethine, Pentaerythritol Tetraacetate, α-phenybutyramide, Priozadil, Probucol, B-Sitosterol, Sultosilic Acid, Piperazine Salt, Tiadenol, Triparanol and Xenbucin, and combinations thereof. The first and second amounts together comprise a therapeutically effective amount. Further, the combination therapy can also include HMG CoA reductase inhibitors such as those described in U.S. patent application Ser. No. 09/311,402 filed on May 13, 1999 entitled, Combination Therapy for Treating Hypercholesterolemia, by C. Huval, S. Holmes-Farley, J. Petersen and P. Dhal, the entire content of which is incorporated herein by reference.

The invention further relates to pharmaceutical compositions useful for the treatment of hypercholesterolemia and atherosclerosis, and for reducing serum cholesterol. The pharmaceutical compositions comprise a combination of a first amount of an unsubstituted polydiallylamine polymer compound and a second amount of a cholesterol-lowering agent selected from the group consisting of fibrates, nicotinic acid and derivatives thereof, and other cholesterol-lowering agents such as Acifran, Azacosterol, Benfluorex, β-Benzalbutyramide, Carnitine, Chondroitin Sulfate, Clomestrone, Detaxtran, Dextran Sulfate Sodium, 5,8,11,14,17-Eicosapentaenoic Acid, Eritadenine, Furazabol, Meglutol, Melinamide, Mytatrienediol, Ornithine, γ-Oryzanol, Pantethine, Pentaerythritol Tetraacetate, α-phenybutyramide, Priozadil, Probucol, B-Sitosterol, Sultosilic Acid, Piperazine Salt, Tiadenol, Triparanol and Xenbucin, and combinations thereof. The first and second amounts together comprise a therapeutically effective amount. Further, the pharmaceutical compositions can also include HMG CoA reductase inhibitors such as those described in U.S. patent application Ser. No. 09/311,402 filed on May 13, 1999 entitled, Combination Therapy for Treating Hypercholesterolemia, by C. Huval, S. Holmes-Farley, J. Petersen and P. Dhal, the entire content of which is incorporated herein by reference. The pharmaceutical compositions of the present invention may optionally contain a pharmaceutically acceptable carrier.

The unsubstituted polydiallylamine polymers are characterized by one or more monomeric units of the formulae:

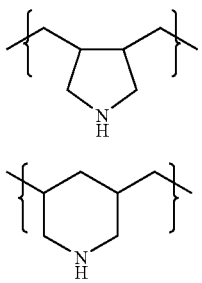

or a combination thereof and salts thereof. The polymer can be characterized by the substantial absence of one or more alkylated amine monomers and/or the substantial absence of one or more trialkylammonium alkyl groups. The polymers are non-absorbable and optionally crosslinked. In preferred embodiments, the polymer is crosslinked by means of a multifunctional crosslinking agent. The polymer can also be characterized as being linear or branched.

Each compound is present in the pharmaceutical composition in an amount which in combination with the other provides a therapeutically effective amount. The pharmaceutical composition can include one or more of each compound.

Other features and advantages will be apparent from the following description of the preferred embodiments thereof and from the claims.

DETAILED DESCRIPTION OF THE INVENTION

The features and other details of the invention will now be more particularly described and pointed out in the claims. It will be understood that the particular embodiments of the invention are shown by way of illustration and not as limitations of the invention. The principal features of the invention can be employed in various embodiments without departing from the scope of the present invention.

The invention provides methods for treating hypercholesterolemia and atherosclerosis, and reducing serum cholesterol in a mammal. The methods of the invention comprise administering to a mammal a first amount of a bile acid sequestrant compound which is an unsubstituted polydiallylamine polymer and a second amount of a cholesterol-lowering agent selected from the group consisting of fibrates, nicotinic acid and derivatives thereof, and other cholesterol-lowering agents such as Acifran, Azacosterol, Benfluorex, β-Benzalbutyramide, Carnitine, Chondroitin Sulfate, Clomestrone, Detaxtran, Dextran Sulfate Sodium, 5,8,11,14,17-Eicosapentaenoic Acid, Eritadenine, Furazabol, Meglutol, Melinamide, Mytatrienediol, Omithine, γ-Oryzanol, Pantethine, Pentaerythritol Tetraacetate, α-phenybutyramide, Priozadil, Probucol, B-Sitosterol, Sultosilic Acid, Piperazine Salt, Tiadenol, Triparanol and Xenbucin, and combinations thereof. The first and second amounts together comprise a therapeutically effective amount. Further, the combination therapy can include HMG CoA reductase inhibitors such as those described in U.S. patent application Ser. No. 09/311, 402 filed on May 13, 1999 entitled, Combination Therapy for Treating Hypercholesterolemia, by C. Huval, S. Holmes-Farley, J. Petersen and P. Dhal, the entire content of which is incorporated herein by reference.

As used herein, the term "cholesterol-lowering agent" is intended to mean an agent selected from the group consisting of fibrates, nicotinic acid and derivatives thereof, and the following cholesterol-lowering agents: Acifran, Azacosterol, Benfluorex, β-Benzalbutyramide, Camitine, Chondroitin Sulfate, Clomestrone, Detaxtran, Dextran Sulfate Sodium, 5,8,11,14,17-Eicosapentaenoic Acid, Eritadenine, Furazabol, Meglutol, Melinamide, Mytatrienediol, Omithine, γ-Oryzanol, Pantethine, Pentaerythritol Tetraacetate, a-phenybutyramide, Priozadil, Probucol, B-Sitosterol, Sultosilic Acid, Piperazine Salt, Tiadenol, Triparanol and Xenbucin, and combinations thereof.

As used herein, the term "therapeutically effective amount" is intended to qualify the combined amount of the first and second compounds in the combination therapy. The combined amount will achieve the desired biological response. In the present invention, the desired biological response can be the treatment of hypercholesterolemia, the treatment of atherosclerosis and/or a reduction of serum cholesterol. The mammal can be a human.

The unsubstituted polydiallylamine polymers are characterized by one or more monomeric units of the formulae:

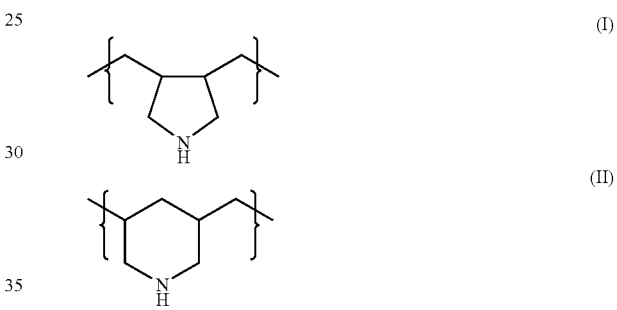

or a combination thereof and salts thereof. The polymer can be characterized by the substantial absence of one or more alkylated amine monomers and/or the substantial absence of one or more trialkylammonium alkyl groups. The polymers are non-absorbable and optionally crosslinked. In preferred embodiments, the polymer is crosslinked by means of a multifunctional crosslinking agent. The polymer can also be characterized as being linear or branched.

As described above, the polymers employed in the method and pharmaceutical composition described herein comprise non-absorbable, optionally cross-linked polydiallylamines characterized by the formula above. Importantly, the polymers can be characterized by the substantial absence of substituted or unsubstituted alkyl substituents on the amino group of the monomer, such as obtained in the alkylation of an amine polymer. That is, the polymer can be characterized in that the polymer is substantially free of alkylated amine monomers.

The polymer can be a homopolymer or a copolymer. Where copolymers are manufactured with a diallylamine monomer, the comonomers are preferably inert, non-toxic and/or possess bile acid sequestration properties. Suitable examples of additional comonomers include substituted and unsubstituted acrylate, substituted and unsubstituted acrylamide, substituted and unsubstituted methacrylate, substituted and unsubstituted methacrylamide, allylamine, triallylamine, allyl alcohol, substituted and unsubstituted vinyl amine and substituted and unsubstituted vinyl alcohol. In one embodiment, the additional monomer is sulfur dioxide. Preferably, the monomers are aliphatic. Most preferably, the polymer is a homopolymer, i.e. a homopolydiallylamine.

Preferably, the polymer is rendered water-insoluble by branching and/or crosslinking. The cross-linking agent can be characterized by functional groups which react with the amino group of the monomer. Alternatively, the crosslinking group can be characterized by two or more vinyl groups which undergo free radical polymerization with the amine monomer. Suitable multifunctional co-monomers include triallylamine, tetraallylammonium salts, bis(diallylamine)s (such as alkylene bis(diallylamine)s), diacrylates, triacrylates and tetraacrylates, dimethacrylates, diacrylamides, diallylacrylamide and di(methacrylamides). Specific examples include ethylene bis(diallylamine), hexamethylene bis(diallylamine), ethylene glycol diacrylate, propylene glycol diacrylate, butylene glycol diacrylate, ethylene glycol dimethacrylate, butylene glycol dimethacrylate, methylene bis(methacrylamide), ethylene bis(acrylamide), ethylene bis(methacrylamide), ethylidene bis(acrylamide), ethylidene bis(methacrylamide), pentaerythritol tetraacrylate, trimethylolpropane triacrylate, bisphenol A dimethacrylate, and bisphenol A diacrylate. Other suitable multifunctional monomers include polyvinylarenes, such as divinylbenzene.

The polymer can alternatively be crosslinked by bridging units which link amino groups on adjacent polymer strands. Suitable bridging units include straight chain or branched, substituted or unsubstituted alkylene groups, diacylalkylene groups, diacylarene groups and alkylene bis(carbamoyl) groups. Examples of suitable bridging units include —$(CH_2)_n$—, wherein n is an integer from about 2 to about 20; —$CH_2$—$CH(OH)$—$CH_2$—; —$C(O)CH_2CH_2C(O)$—; —$CH_2$—$CH(OH)$—$O$—$(CH_2)_n$—$O$—$CH(OH)$—$CH_2$—, wherein n is 2 to about 4; —$C(O)$—$(C_6H_2(COOH)_2)$—$C(O)$— and —$C(O)NH(CH_2)_p NHC(O)$— wherein p is an integer from about 2 to about 20.

Examples of suitable crosslinking agents include acryloyl chloride, epichlorohydrin, butanedioldiglycidyl ether, ethanedioldiglycidyl ether, and dimethyl succinate.

A preferred crosslinking agent is epichlorohydrin because of its high availability and low cost. Epichlorohydrin is also advantageous because of its low molecular weight and hydrophilic nature, increasing the water-swellability of the polyamine.

The level of crosslinking makes the polymers insoluble and substantially resistant to absorption and degradation, thereby limiting the activity of the polymer to the gastrointestinal tract. Thus, the compositions are non-systemic in their activity and will lead to reduced side-effects in the patient. Typically, the cross-linking agent is present in an amount from about 0.5-50% (more preferably about 0.5-30% and most preferably about 2-20%) by weight, based upon total weight of monomer plus crosslinking agent.

When used in a non-crosslinked form, polymers of use in the present method are, preferably, of a molecular weight which enables them to reach and remain in the gastrointestinal tract for a sufficient period of time to bind a significant amount of one or more bile acids. These polymers should, thus, be of sufficiently high molecular weight to resist, partially or completely, absorption from the gastrointestinal tract into other regions of the body. The resulting polymer/bile salt complex should then be excreted from the body. Suitable linear (non-crosslinked) polymers have molecular weights which range from about 2,000 Daltons to about 500,000 Daltons, preferably from about 5,000 Daltons to about 150,000 Daltons. Crosslinked polymers, however, are not generally characterized by molecular weight. The crosslinked polymers discussed herein should be sufficiently crosslinked to resist adsorption from the gastrointestinal tract.

As described above the polymer can be administered in the form of a salt, or as a partial salt. By "salt" it is meant that the nitrogen groups in all or some of the repeat units are protonated to create a positively charged nitrogen atom associated with a negatively charged counterion.

The anionic counterions can be selected to minimize adverse effects on the patient, as is more particularly described below. Examples of suitable counterions include $Cl^-$, $Br^-$, $CH_3OSO_3^-$, $HSO_4^-$, $SO_4^{2-}$, nitrate, $HCO_3^-$, $CO_3^{2-}$, acetate, lactate, phosphate, hydrophosphate, methanesulfonate, fumarate, malate, pyruvate, malonate, benzoate, glucuronate, oxalate, acetylglycinate, succinate, propionate, butyrate, ascorbate, citrate, tartrate, maleate, folate, an amino acid derivative, a nucleotide, a lipid, or a phospholipid. The counterions can be the same as, or different from, each other. For example, the reaction product can contain two different types of counterions.

Polymers of use in the present method can be prepared using techniques known in the art of polymer synthesis (see for example, Shalaby et al., ed., *Water-Soluble Polymers*, American Chemical Society, Washington D.C. (1991)). For example, the appropriate monomer(s) can be polymerized by methods known in the art, for example, via a free radical addition process. In this case the polymerization mixture includes a free-radical initiator, such as a free radical initiator selected from among those which are well known in the art of polymer chemistry. Suitable free-radical initiators include azobis(isobutyronitrile), azobis(4-cyanovaleric acid), azobis (amidinopropane) dihydrochloride, potassium persulfate, ammonium persulfate and potassium hydrogen persulfate. The free radical initiator is preferably present in the reaction mixture in an amount ranging from about 0.1 mole percent to about 5 mole percent relative to the monomer.

The polymer can be crosslinked, for example, by including a multifunctional co-monomer as the crosslinking agent in the reaction mixture. A multifunctional co-monomer can be incorporated into two or more growing polymer chains, thereby crosslinking the chains. Suitable multifunctional co-monomers include those discussed above.

The polymers can also be crosslinked subsequent to polymerization by reacting the polymer with one or more crosslinking agents having two or more functional groups, such as electrophilic groups, which react with amine groups to form a covalent bond. Crosslinking in this case can occur, for example, via nucleophilic attack of the polymer amino groups on the electrophilic groups. This results in the formation of a bridging unit which links two or more amino nitrogen atoms from different polymer strands. Suitable crosslinking agents of this type include compounds having two or more groups selected from among acyl-X, epoxide, and alkyl-X, wherein X is a suitable leaving group, such as a halo, tosyl, mesyl, acyl or glycidyl group. Examples of such compounds include epichloro-hydrin, succinyl dichloride, butanedioldiglycidyl ether, ethanedioldiglycidyl ether, pyromellitic dianhydride and dihaloalkanes. The crosslinking agent can also be an α,ω-alkylene diisocyanate, for example $OCN(CH_2)_p NCO$, wherein p is an integer from about 2 to about 20.

The polymer can also be crosslinked using a crosslinking agent which incorporates one functional group which incorporates into the polymerizing chain and a second functional group which can react with amine groups in a second polymer chain. Examples include glycidyl methacrylate, glycidyl acrylate, acryloyl chloride, methacryloyl chloride, 3-bromopropylacrylate, 3-bromopropylmethyl-diallylammonium chloride, and 3-chloropropyldiallylamine.

The Fibrates useful in the present invention are listed in Table 1. The Patent Nos. listed in Table 1 are incorporated herein by reference.

TABLE 1

| FIBRATES | ALTERNATIVE NAME | PATENT NO. |
|---|---|---|
| Beclobrate | Beclipur; Turec | U.S. Pat. No. 4,483,999 |
| Bezafibrate | Benfizal; Benzalip; Bezatol; Cedur; Difaterol | U.S. Pat. No. 3,781,328 |
| Binifibrate | | |
| Ciprofibrate | Ciprol; Lipanor; Modalim | U.S. Pat. No. 3,948,973 |
| Clinofibrate | Lipoclin | U.S. Pat. No. 3,716,583 |
| Clofibrate | Amotril; Anparton; Apolan; Artevil; Ateculon; Arteriosan; Atheropront; Atromidin; Atromid-S; Biosclercan; Claripex; Clobren-SF; Clofinit; CPIB; Hyclorate; Liprinal; Neo-Atromid; Normet; Normolipol; Recolip; Regelan; Serotinex; Sklerolip; Skleromexe; Sklero-Tablinen; Ticlobran; Xyduril | U.S. Pat. No. 3,262,850 |
| Clofibric Acid | | GB 860,303 |
| Etofibrate | | U.S. Pat. No. 3,723,446 |
| Fenofibrate | Ankebin; Elasterin; Fenobrate; Fenotard; Lipanthyl; Lipantil; Lipidil; Lipoclar; Lipofene, Liposit; Lipsin; Nolipax; Procetoken; Protolipan; Secalip | U.S. Pat. No. 4,058,552 |
| Gemfibrozil | Decrelip; Genlip; Gevilon; Lipozid; Lipur; Lopid | U.S. Pat. No. 3,674,836 |
| Nicofibrate | | U.S. Pat. No. 3,369,025 |
| Pirifibrate | | |
| Ronifibrate | Bratenol | U.S. Pat. No. 3,971,798 |
| Simifibrate | Cholesolvin; Liposolvin | U.S. Pat. No. 3,494,957 |
| Theofibrate | Duolip | U.S. Pat. No. 3,984,413 |

The nicotinic acid and derivatives thereof which are useful in the present invention are Nicotinic Acid, also referred to as Niacin available, for example, as NICOLAR® tablets and Nicotinic acid derivatives: Acipimox, Aluminum Nicotinate, Niceritrol, Nicoclonate, Nicomol and Oxiniacic Acid.

Thyroid hormones and analogs useful in the present invention include, but are not limited to, Etiroxate, Thyropropic Acid and Thyroxine.

Other cholesterol-lowering agents useful in the present invention include, Acifran, Azacosterol, Benfluorex, β-Benzalbutyramide, Carnitine, Chondroitin Sulfate, Clomestrone, Detaxtran, Dextran Sulfate Sodium, 5,8,11,14,17-Eicosapentaenoic Acid, Eritadenine, Furazabol, Meglutol, Melinamide, Mytatrienediol, Ornithine, γ-Oryzanol, Pantethine, Pentaerythritol Tetraacetate, α-phenybutyramide, Priozadil, Probucol, B-Sitosterol, Sultosilic Acid, Piperazine Salt, Tiadenol, Triparanol and Xenbucin.

The invention further relates to pharmaceutical compositions useful for the treatment of hypercholesterolemia and atherosclerosis, and for reducing serum cholesterol. The pharmaceutical compositions comprise a combination of a first amount of an unsubstituted polydiallylamine polymer compound and a second amount of a cholesterol-lowering agent selected from the group consisting of fibrates, nicotinic acid and derivatives thereof, and other cholesterol-lowering agents such as Acifran, Azacosterol, Benfluorex, β-Benzalbutyramide, Carnitine, Chondroitin Sulfate, Clomestrone, Detaxtran, Dextran Sulfate Sodium, 5,8,11,14,17-Eicosapentaenoic Acid, Eritadenine, Furazabol, Meglutol, Melinamide, Mytatrienediol, Ornithine, γ-Oryzanol, Pantethine, Pentaerythritol Tetraacetate, α-phenybutyramide, Priozadil, Probucol, B-Sitosterol, Sultosilic Acid, Piperazine Salt, Tiadenol, Triparanol and Xenbucin, and combinations thereof. The first and second amounts together comprise a therapeutically effective amount. Further, the pharmaceutical compositions can include HMG CoA reductase inhibitors such as those described in U.S. patent application Ser. No. 09/311,402 filed on May 13, 1999 entitled, Combination Therapy for Treating Hypercholesterolemia, by C. Huval, S. Holmes-Farley, J. Petersen and P. Dhal, the entire content of which is incorporated herein by reference. The pharmaceutical compositions of the present invention may optionally contain a pharmaceutically acceptable carrier. The first and second amounts of said compounds comprise a therapeutically effective amount.

In practicing the methods of the invention, combination therapy refers to administration of a first amount of an unsubstituted polydiallylamine polymer compound and a second amount of a cholesterol-lowering agent, as defined herein, and/or an HMG CoA reductase inhibitor to treat hypercholesterolemia and atherosclerosis, and reduce serum cholesterol. Administration in combination therapy encompasses co-administration of the first and second amounts of the compounds of the combination therapy in a single substantially simultaneous manner, such as in a single capsule or tablet having a fixed ratio of first and second amounts, or in multiple, separate capsules or tablets for each. In addition, such administration also encompasses use of each compound in a sequential manner.

Administration, of the cholesterol-lowering agent, and HMG CoA reductase inhibitor, when present, in combination therapy, may be accomplished by oral route, or by intravenous, intramuscular, subcutaneous injections or a combination thereof. The cholesterol-lowering agent and HMG CoA reductase inhibitor of the combination can be in the form of a bolus, or in the form of aqueous or non-aqueous isotonic sterile injection solutions or suspensions. These solutions and suspensions may be prepared from sterile powders or granules having one or more pharmaceutically-acceptable carriers or diluents, for example, saline, dextrose, water or a combination thereof, or a binder such as gelatin or hydroxypropylmethyl cellulose, together with one or more of a lubricant, preservative, surface active or dispersing agent.

For oral administration, all compounds used in the combination therapy can be in the form of, for example, a tablet, capsule, suspension, or liquid. Capsules, tablets, and the like can be prepared by conventional methods well known in the art. The compounds are preferably made in the form of a dosage unit containing a specified amount of the compound. Examples of dosage units are tablets or capsules.

Pharmaceutical compositions for use in the treatment methods of the present invention can be administered in oral form for all compounds of the composition, or by intravenous administration for the cholesterol-lowering agent and HMG CoA reductase inhibitor, when present. Oral administration of the pharmaceutical composition comprising the compounds of the combination therapy is preferred. Dosing for oral administration can be with a regimen calling for single daily dose, or for a single dose every other day, or for multiple, spaced doses throughout t the day.

The unsubstituted polydiallylamine polymer compound and the cholesterol-lowering agent which comprise the pharmaceutical composition can be administered simultaneously, either in a combined dosage form or in separate dosage forms intended for substantially simultaneous oral administration. The agents which make up the pharmaceutical composition may also be administered sequentially, with either compound being administered by a regimen calling for two-step ingestion. Thus, a regimen may call for sequential administration of the compound with spaced-apart ingestion of the separate, active compounds. The time period between the multiple ingestion steps may range from a few minutes to several hours, depending upon the properties of each compound such as potency, solubility, bioavailability, plasma half-life and kinetic profile of the compound, as well as depending upon the age and condition of the patient. The compounds of the pharmaceutical composition whether administered simultaneously, substantially simultaneously, or sequentially, can involve a regimen calling for administration of the unsubstituted polydiallylamine polymer by oral route and cholesterol-lowering agent by intravenous route. Whether the agents of the pharmaceutical composition are administered by oral or intravenous route, separately or together, each compound can be contained in a suitable pharmaceutical formulation of pharmaceutically-acceptable excipients, diluents or other formulations as described above.

Treatment Regimen

The dosage regimen to treat hypercholesterolemia and atherosclerosis and reduce plasma cholesterol with the combination therapy and pharmaceutical compositions of the present invention is selected in accordance with a variety of factors. These include the type, age, weight, sex, diet, and medical condition of the patient, the severity of the disease, the route of administration, pharmacological consideration such as the activity, efficacy, pharmacokinetics and toxicology profiles of the particular compound employed, whether a drug delivery system is utilized, and whether the compound is administered as part of a drug combination. Thus, the dosage regimen actually employed may vary widely and therefore deviate from the preferred dosage regimen set forth above.

Initial treatment of a patient suffering from a hyperlipidemic condition such as hypercholesterolemia and atherosclerosis can begin with the dosages indicated above. Treatment should generally be continued as necessary over a period of several weeks to several months or years until the condition has been controlled or eliminated. Patients undergoing treatment with the compounds or compositions disclosed herein can be routinely monitored by, for example, measuring serum LDL and total cholesterol levels by any of the methods well known in the art, to determine the effectiveness of the combination therapy. Continuous analysis of such data permits modification of the treatment regimen during therapy so that optimal effective amounts of each type of agent are administered at any point in time, and so that the duration of treatment can be determined as well. In this way, the treatment regimen/dosing schedule can be rationally modified over the course of therapy so that the lowest amount of unsubstituted polydiallylamine bile acid sequestrant and cholesterol-lowering agent, as defined herein, which together exhibit therapeutic effectiveness, is administered and so that administration is continued only so long as is necessary to successfully to treat the hyperlipidemic condition such as hypercholesterolemia and atherosclerosis.

A potential advantage of the combination therapy disclosed herein may be reduction of the first amount of unsubstituted polydiallylamine bile acid sequestrant, second amount of other cholesterol-lowering agent or both, and/or HMG Co-A reductase inhibitor, when present, effective in treating hyperlipidemic conditions such as atherosclerosis and hypercholesterolemia, and in reducing serum cholesterol.

In the case of fibrates, the dose can range from about 0.02 g/day to about 2.5 g/day, more particularly from about 0.5 g to about 2.0 g, most particularly from about 1 g/day to about 2 g/day, or any other dose, depending upon the specific fibrate, as is normally employed in the art, for example, as indicated in the Physician's Desk Reference and The Merck Index (Twelfth Edition), the contents of both of which are incorporated herein by reference.

The unsubstituted polydiallylamine bile acid sequestrant compound can be administered in an amount from about 1 mg/kg/day to about 10 g/kg/day, preferably from about 1 mg/kg/day to about 1 g/kg/day, more preferably from about 1 mg/kg/day to about 200 mg/kg/day, and most preferably from about 1 mg/kg/day to about 100 mg/kg/day.

In the case of niacin, and niacin/nicotinic acid derivatives the dose can range from about 0.5 g/day to about 12 g/day, more particularly from about 1 g to about 8 g/day, or any other dose, depending upon the specific agent, as is normally employed in the art, for example, as indicated in the Physician's Desk Reference and The Merck Index (Twelfth Edition), the contents of both of which are incorporated herein by reference.

For the thyroid hormones and analogs, Etiroxate, Thyropropic Acid and Thyroxine, the dose would be that normally employed in the art, for example, as indicated in the Physician's Desk Reference and The Merck Index (Twelfth Edition), the contents of both of which are incorporated herein by reference.

With regard to the other cholesterol-lowering agents which include, Acifran, Azacosterol, Benfluorex, β-Benzalbutyramide, Camitine, Chondroitin Sulfate, Clomestrone, Detaxtran, Dextran Sulfate Sodium, 5,8,11,14,17-Eicosapentaenoic Acid, Eritadenine, Furazabol, Meglutol, Melinamide, Mytatrienediol, Omithine, γ-Oryzanol, Pantethine, Pentaerythritol Tetraacetate, α-phenybutyramide, Priozadil, Probucol, B-Sitosterol, Sultosilic Acid, Piperazine Salt, Tiadenol, Triparanol and Xenbucin, the dose would be that normally employed in the art, for example, as indicated in the Physician's Desk Reference and The Merck Index (Twelfth Edition), the contents of both of which are incorporated herein by reference.

The particular dosage will depend on the individual patient (e.g., the patient's weight and the extent of bile salt removal required). The polymer can be administered either in hydrated or dehydrated form, and can be flavored or added to a food or drink, if desired, to enhance patient acceptability. Additional ingredients such as other bile acid sequestrants, drugs for treating hypercholesterolemia, atherosclerosis or other related indications, or inert ingredients, such as artificial coloring agents can be added as well.

The first and second amounts of the compounds of the combination therapy can be administered by any dual combination of oral/oral, oral/parenteral, or parenteral/parenteral route, respectively.

Examples of suitable forms for administration include pills, tablets, capsules, and powders (e.g., for sprinkling on food). The pill, tablet, capsule, or powder can be coated with a substance capable of protecting the composition from disintegration in the esophagus but will allow disintegration of the composition in the stomach and mixing with food to pass into the patient's small intestine. The polymer can be administered alone or in combination with a pharmaceutically acceptable carrier, diluent or excipient substance, such as a solid, liquid or semi-solid material. Examples of suitable carriers, diluents and excipients include lactose, dextrose, sucrose, sorbitol, mannitol, starches, gum acacia, alginates, tragacanth, gelatin, calcium silicate, cellulose e.g., magnesium carbonate or a phospholipid with which the polymer can form a micelle.

The invention will now be described more specifically by the examples.

EXAMPLE 1

Preparation of POLY(DIALLYLAMMONIUM Chloride)

Concentrated hydrochloric acid (507.0 g; 37%) was charged to a 5L, 3-neck round bottomed flask and agitated with a mechanical stirrer. The flask was cooled to <5° C. with an ice bath. Diallylamine (635.0 ml) was added dropwise to the stirring hydrochloric acid over a three hour period using an addition funnel capped with a pierced rubber septum. The stirring solution temperature was maintained at <10° C. After the addition was completed, the ice bath was removed and the mixture was allowed to warm to room temperature. Concentrated hydrochloric acid (7.3 g) was added to the solution. Water (368.7 g) was added to the solution and it was allowed to sit overnight.

The stirring solution was purged with nitrogen gas for 30 minutes at room temperature. 2,2'-Azobis[2-amidinopropane]dihydrochloride (6.87 g) was added as 34.4 g of a 20% aqueous solution. The solution was heated to 60°-80° C. for six and one-half hours. 2,2'-Azobis[2-amidinopropane] dihydrochloride (6.87 g) was added as a 20% aqueous solution. The solution was stirred and heated overnight (16 hours).

2,2'-Azobis[2-amidinopropane]dihydrochloride (6.87 g) was added as a 20% aqueous solution. The solution was stirred and heated for another 16 hours, then cooled to room temperature.

Sodium hydroxide (53.8 g) was dissolved in $H_2O$ (2156 mL). The polydiallylamine.HCl solution was then added to the sodium hydroxide solution and agitated with a mechanical stirrer until dissolved. Concentrated hydrochloric acid (49.8 g; 37%) was added.

EXAMPLE 2

Synthesis of Polydiallylamine

A solution of 39.3 g of an aqueous solution (68 wt %) of diallylammonium hydrochloride, 5.3 g of an aqueous solution (73 wt %) of triallylamine hydrochloride and 0.9 g of 2,2'-azobis(2-amidinopropane)dihydrochloride was bubbled with a slow stream of nitrogen for 30 minutes. While stirring, this reaction mixture was added to a solution of 7 g of polyvinylacetate in 300 mL of toluene. The resulting mixture was stirred at room temperature for 45 minutes under nitrogen atmosphere. While stirring, the temperature of the reaction mixture was raised to 60 C and was held at this temperature for 24 hours. The reaction mixture was allowed to cool to room temperature and the polymer particles were collected by filtration. While in the funnel, the filtered particles were successively washed with 300 mL of toluene and 500 mL of methanol. The polymer particles were suspended in 500 mL of methanol, stirred for 50 minutes, and filtered. Subsequently, the particles were suspended in 400 mL of deionized water, stirred for 30 minutes and filtered. The filtered particles were dried at 60 C for 24 hr to yield 15 g of the polymer.

EXAMPLE 3

Cross-Linked Polydiallylamine

The polymer solution of Example 1 was crosslinked at 30 mole % as follows:

Epichlorohydrin (31.61 mL) was added to 900.0 g of the neutralized polymer solution in a glass beaker, agitated with a magnetic stirrer and covered with polyvinyl film. The gel was allowed to cure for 22 hours. The solid gel was then ground using a grinder. The ground polymer was washed in a static bed manner using a large plastic Buchner funnel lined with filter paper. A second piece of filter paper, perforated with holes, was placed on top of the polymer cake to prevent disturbing the cake when adding wash water. Fresh deionized $H_2O$ (14 L) was added to the top of the cake and drained under vacuum. The washed polymer was then transferred to glass drying trays and dried in a 60° C. forced air oven for several days. The final dry weight was 176.2 g.

EXAMPLE 4

Crosslinked Polydiallylamine

Using the same procedure as in Example 3, the neutralized polymer solution was crosslinked at 20 mole %. Epichlorohydrin (21.07 mL) was added to 900.0 g of the neutralized polymer solution. The final dry weight was 163.3 g.

EXAMPLE 5

Crosslinked Polydiallylamine

Using the same procedure as in Example 3, the neutralized polymer solution was crosslinked at 10 mole %. Epichlorohydrin (10.54 mL) was added to 900.0 g of the neutralized polymer solution. The final dry weight was 164.2 g.

EXAMPLE 6

Crosslinked Polydiallylamine

Using the same procedure as in Example 3, the neutralized polymer solution was crosslinked at 4.5 mole %. Epichlorohydrin (4.74 mL) was added to 900.0 g of the neutralized polymer solution. The final dry weight was 176.2 g.

EXAMPLE 7

Copolymer of Diallylamine and Methylenebisacrylamide

A solution of diallylammonium chloride (73.53 g of 68% aqueous solution), methylenebisacrylamide (2.93 g, 0.019 mol), 2,2'-azobis(2-amidinopropane) dihydrochloride (V50) (0.5 g) and water (27 mL) was heated at 70° C. under a nitrogen atmosphere. Water (100 mL) was added after 15 minutes of reaction. An additional 0.5 g of V50 was added after 3 hours and again after 4 more hours. After keeping the reaction at 70 C for a total of 72 hr, it was cooled to room temperature. The resulting material was filtered and washed with 2 M NaCl (400 mL), and filtered and washed with water (2.5 L) and filtered again. The washed polymer was dried at 60° C. in a forced-air oven gave 18.8 g of a solid (0.36 g/g yield, IPS=18.4)

EXAMPLE 8

Copolymer of Diallylamine and Acrylamide

A solution of diallylammonium chloride (73.53 g of 68% aqueous solution), methylenebisacrylamide (2.93 g, 0.019 mol), 2,2'-azobis(2-amidinopropane) dihydrochloride (0.5 g) and water (27 mL) was heated at 70° C. under a nitrogen atmosphere for 3 days. Water (100 mL) was added after the first 15 minutes of reaction. 2,2'-Azobis(2-amidinopropane) dihydrochloride (0.5 g) was added after 3 hours and 7 hours. The resulting material was filtered and washed with 2 M NaCl (400 mL) and water (2.5L). The washed polymer was dried at 60° C. in a forced-air oven to give 18.8 g of a solid.

EXAMPLE 9

Copolymer of Diallylamine, Acrylamide and Methylenebisacrylamide

A solution of diallylammonium chloride (14.7 g of 68% aqueous), acrylamide (5.33 g), methylenebisacrylamide (2.31 g), MeOH (50 mL), and 2,2'-azobis(2-amidinopropane) dihydrochloride (0.07 g of an 18.8% solution of water) was heated at 65° C. under a nitrogen atmosphere for 20 hours. The resulting material was suspended in methanol (500 mL), stirred for 15 minutes and filtered. This methanol wash was repeated twice more. The washed polymer was suspended in water (500 mL) and this mixture was acidified with concentrated HCl to pH 2.4. Filtration, and drying at 60° C. in a forced-air oven gave 9.8 g of a solid.

EXAMPLE 10

Copolymer of Diallylamine, a Functionalized Acrylic Ester and an Acrylic Ester Cross-Linking Monomer A solution of diallylammonium chloride (14.7 g of 68% aqueous), 2-hydroxyethylmethacrylate (9.76 g), ethyleneglycol dimethacrylate (2.97 g), MeOH (25 mL), and 2,2'-azobis(2-amidinopropane) dihydrochloride (0.07 g of an 18.8% aqueous solution) was heated at 65° C. under a nitrogen atmosphere for 20 hours. The resulting material was suspended in methanol (500 mL), stirred for 15 minutes and filtered. The polymer was similarly washed three times with water (500 mL). This methanol wash and filtration were repeated twice more. The washed polymer was suspended in water (500 mL) and this mixture was acidified with concentrated HCl to pH 2.1. Filtration and drying at 60° C. in a forced-air oven gave 13.9 g of a solid.

EXAMPLE 11

Copolymer of Diallylamine, a Functionalized Acrylic Ester and an Acrylic Ester Cross-Linking Monomer A solution of diallylammonium chloride (22.06 g of a 68% aqueous solution), tetrahydrofurfuryl methacrylate (18.72 g), ethyleneglycol dimethacrylate (4.36 g) and 2,2'-azobis(2-amidinopropane) dihydrochloride (2.03 g of an 18.8% aqueous solution) was heated at 65° C. under a nitrogen atmosphere for 24 hours. The resulting material was suspended in methanol (300 mL), stirred 15 minutes and filtered. This methanol wash and filtration was repeated twice more. The polymer was similarly washed three times with water (500 mL). The material was suspended in water (500 mL) and this mixture was acidified with concentrated HCl to pH 2.0. Filtration, and drying at 60° C. in a forced-air oven gave 19.9 g of a solid.

EXAMPLE 12

Copolymer of Diallylamine and Glycidylmethacrylate

A solution of diallylammonium chloride (29.42 g of a 68% aqueous solution), glycidylmethacrylate (2.13 g), MeOH (25 mL), and 2,2'-azobis(2-amidinopropane) dihydrochloride (1.18 g of an 18.8% aqueous solution) was heated at 65° C. under a nitrogen atmosphere for 12 hours. After cooling to room temperature, methanol (25 mL) was added and the pH of the solution was adjusted to 10 with the addition of 50% aqueous NaOH, and allowed to stir at room temperature. The reaction solution turned to a solid mass after about 2 hours, and was allowed to stand for 22 hours. The resulting gel, was suspended in MeOH (300 mL), stirred and filtered. This methanol wash and filtration were repeated twice more. The polymer was then suspended in water (1 L). Concentrated HCl was added to this suspension until pH 2.0 and stirred 0.5 hours. Filtration and drying in a forced-air oven at 60° C. gave 6.0 g of a solid.

EXAMPLE 13

Copolymer of Allylamine, Diallylamine Triallylamine and a BIS(DIALLYLAMINO)ALKYLENE Salt A solution of allylammonium chloride (25.0 g of a 60% aqueous solution), diallylammonium chloride (66.81 g of a 67% aqueous solution), triallylammonium chloride (40.87 g of a 68% aqueous solution), 1,6-bis(diallylmethylammoniium) hexane dibromide (5.0 g), and 2,2'-azobis(2-amidinopropane) dihydrochloride (4.28 g of a 20% aqueous solution), was heated at 55° C. under a nitrogen atmosphere for 18 hours and at 80° C. for 2 hours. After cooling to room temperature, the gel was suspended in MeOH (500 mL), stirred 15 minutes and filtered. This method was repeated. The polymer was suspended in water (1.0 L) and stirred at least 15 minutes and filtered. After drying in a 60° C. forced-air oven, 31.9 g of solid was isolated.

EXAMPLE 14

Copolymer of Allylamine and Diallylamine

A solution of allylammonium chloride (54.71 g of a 57% aqueous solution), diallylammonium chloride (132.96 g of a 67% aqueous solution), and 2,2'-azobis(2-amidinopropane) dihydrochloride (6.01 g of a 20% aqueous solution), was heated at 55° C. under a nitrogen atmosphere for 36 hours. Another portion of 2,2'-azobis(2-amidinopropane)dihydrochloride (6.01 g of a 20% aqueous solution) was added after the first 18 hours. After cooling to room temperature, the solution was added slowly to IPA (3 L), and the precipitate after decanting the IPA layer, was washed with IPA (3 L) and filtered. The precipitate was dried in a forced-air oven at 60° C. to afford 106.9 g of a solid.

EXAMPLE 15

Copolymer of Allylamine, Diallylamine and a BIS(DIALLYLAMINO) ALKYLENE

A solution of allylammonium chloride (27.36 g of a 57% aqueous solution), diallylammonium chloride (66.48 g of a 67% aqueous solution), 1,6-bis(diallyl-methylammonium) hexane dibromide (10.0 g), and 2,2'-Azobis(2-amidinopropane) dihydrochloride (3.01 g of a 20% aqueous solution(, was heated at 55° C. under a nitrogen atmosphere for 36 hours. Another portion of 2,2'-Azobis(2-amidino-propane) dihydrochloride (3.01 g of a 20% aqueous solution) was added after the first 18 hours. A gel formed after about 24 hours of heating. After cooling to room temperature, this material was washed with MeOH (500 mL) and filtered three times, as described above. The polymer was then suspended and washed with water (2.5 L). After filtration, the wet material was dried in a forced-air oven at 60° C. to afford 24.8 g of a solid.

EXAMPLE 16

In vivo Testing

Male Golden Syrian Hamsters were group housed in shoe box cages and acclimated for approximately 1 week in our animal facility. Animals were fed rodent chow (brown color) and water ad libitum. The hamsters were then transferred to metabolism cages and housed individually. Following a 24 hour fast (water ad libitum), animals were presented a casein-based purified diet (white color) with 10% fat added plus the drug to be evaluated. Fecal material was collected from 9 hours after the casein-based diet was presented for 39 additional hours. The white fecal pellets (drug-containing casein-based diet) were lyophilized and ground to a homogeneous powder. One gram of the ground fecal pellet was extracted in a solution consisting of methanol and 500 mM aqueous NaOH (4:1; v/v) at 100° C. and 1500 psi for 15 minutes. A 500 µL aliquot of the extract was evaporated and reconstituted in 1500 µL bovine calf serum:0.9% saline (1:1) and analyzed enzymatically, utilizing a test kit for bile acids (Sigma Chemical Co., St. Louis, Mo.) for bile acid concentration.

TABLE 2

| Polymer | Dose (% in feed) | Fecal Bile Acids (µmol/g) |
|---|---|---|
| None | None | 1.34 |
| Example 6 | .10 | 2.19 |
| Example 6 | .15 | 3.44 |
| Example 6 | .20 | 3.72 |
| Example 6 | .25 | 3.48 |
| Cholestyramine | 0.30 | 3.00 |
| Colestipol | 0.30 | 2.81 |

This example shows that crosslinked polydiallylamine is a highly potent bile acid sequestrant, with in vivo activity greater than current commercial products, Colestipol and Cholestyramine.

While this invention has been particularly shown and described with references to preferred embodiments thereof, it will be understood by those skilled in the art that various changes in form and details may be made therein without departing from the scope of the invention encompassed by the appended claims.

What is claimed is:

1. A pharmaceutical composition comprising a unit dosage form of a polydiallylamine homopolymer or a salt thereof, said homopolymer characterized by Formula I Formula II or a combination thereof:

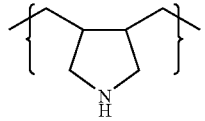 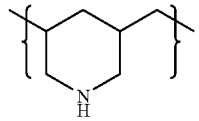

and further characterized in that the polymer is free of alkylated amine monomers, and a pharmaceutically acceptable carrier, wherein said homopolymer is crosslinked by means of a multifunctional crosslinking agent, and said crosslinking agent is present in an amount from about 2.5-20% by weight, based upon the combined weight of monomer and crosslinking agent wherein the unit dosage form is a tablet.

2. The pharmaceutical composition of claim 1 wherein the polymer is crosslinked using epichlorohydrin.

3. A pharmaceutical composition comprising a unit dosage form of a polydiallylamine homopolymer or a salt thereof, said homopolymer characterized by Formula I, Formula II or a combination thereof:

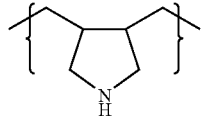 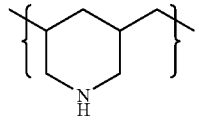

and further characterized in that the polymer is free of alkylated amine monomers, and a pharmaceutically acceptable carrier, wherein said homopolymer is crosslinked by means of a multifunctional crosslinking agent, and said crosslinking agent is present in an amount from about 2.5-20% by weight, based upon the combined weight of monomer and crosslinking agent wherein the unit dosage form is a capsule.

4. The pharmaceutical composition of claim 1, wherein the polydiallylamine homopolymer is in the free base form.

5. The pharmaceutical composition of claim 1, wherein the polydiallylamine homopolymer is a salt or partial salt.

6. The pharmaceutical composition of claim 3, wherein the polydiallylamine homopolymer is in the free base form.

7. The pharmaceutical composition of claim 3, wherein the polydiallylamine homopolymer is a salt or partial salt.

8. The pharmaceutical composition of claim 3, wherein the polymer is crosslinked using epichlorohydrin.

9. The pharmaceutical composition of claim 1, wherein the polydiallylamine homopolymer is water-insoluble.

10. The pharmaceutical composition of claim 3, wherein the polydiallylamine homopolymer is water-insoluble.

* * * * *

UNITED STATES PATENT AND TRADEMARK OFFICE
CERTIFICATE OF CORRECTION

PATENT NO. : 7,638,524 B2  Page 1 of 1
APPLICATION NO. : 10/025184
DATED : December 29, 2009
INVENTOR(S) : Huval et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 575 days.

Signed and Sealed this

Twenty-first Day of December, 2010

David J. Kappos
*Director of the United States Patent and Trademark Office*